United States Patent [19]

Terauchi et al.

[11] Patent Number: 4,960,945

[45] Date of Patent: Oct. 2, 1990

[54] PROCESS FOR THE PRODUCTION OF HALOBENZOPHENONE DERIVATIVES

[75] Inventors: Takashi Terauchi, Kasukabe; Kazuo Yoshida; Yoshihisa Machida, both of Iwaki; Nobuyuki Okubo, Urawa; Yutaka Konai, Machida, all of Japan

[73] Assignee: Kureha Kagaku Kogyo K.K., Japan

[21] Appl. No.: 379,388

[22] Filed: Jul. 13, 1989

[30] Foreign Application Priority Data

Jul. 28, 1988 [JP] Japan ................... 63-186788

[51] Int. Cl.⁵ ............................ C07C 45/27
[52] U.S. Cl. ..................... 568/323; 568/309
[58] Field of Search ........... 568/308, 309, 323

[56] References Cited

U.S. PATENT DOCUMENTS 2,542,985 2/1951 Bond .................... 568/309
4,086,277 4/1978 Onopchenko et al. ............. 568/309

FOREIGN PATENT DOCUMENTS 58-126829 7/1983 Japan .................... 568/309

OTHER PUBLICATIONS

Article by J. Forrest et al., *Journal of the Chemical Society*, (1946), pp. 333–339.
Article by H. L. Bradlow et al., *Journal of the American Chemical Society*, vol. 69, No. 3, pp. 477, 662–663.
Article by O. G. Backeberg et al., Journal of the Chemcial Society, 803, (1945), pp. 803–805.

Japanese Patent Application Laid–Open No. 126829/1983, pp. 251–253.

*Primary Examiner*—James H. Reamer
*Attorney, Agent, or Firm*—Lowe, Price, LeBlanc, Becker & Shur

[57] ABSTRACT

The present invention relates to a process for the production of halobenzophenone derivatives represented by the following formula (II):

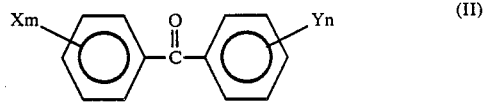

wherein X and Y are the same or different and are independently F, Cl, Br or I, m stands for an integer of from 1 to 4 and n stands for an integer of from 0 to 4. The process comprises oxidizing a compound with an aqueous nitric acid solution having a specific gravity of from 1.32 to 1.47 at 20° C., said compound being represented by the following formula (I):

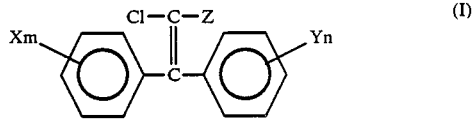

wherein X, Y, m and n have the same meanings as defined above and Z is Cl or H.

2 Claims, No Drawings

PROCESS FOR THE PRODUCTION OF HALOBENZOPHENONE DERIVATIVES

BACKGROUND OF THE INVENTION (1) Field of the Invention:

This invention relates to a process for producing halobenzophenone derivatives useful as monomers for heat-resistant polymers.

(2) Description of the Related Arts:

In recent years, halobenzophenone derivatives have attracted particular attentions as monomers for heat-resistant polymers such as polyether ketones and polythioether ketones. There is hence an outstanding demand for the development of a process permitting their production at a lower cost. Regarding production processes for halobenzophenone derivatives, for example, 4,4'-dichlorobenzophenone, it has been well known to obtain it by oxidation of 1,1-dichloro-2,2-bis(4-chlorophenyl)ethylene. As such processes, oxidation with chromic acid has been reported, for example, by J. Forrest, et al. in J. Chem. Soc., 333 (1946) and by H. L. Bradlow, et al. in J. Amer. Chem. Soc., 69, 662 (1947). In addition, oxidation of 1,1-dichloro-2,2-bis(4-chlorophenyl)ethylene with nitric acid in an organic solvent has been reported by O. G. Backeberg and J. L. C. Marais in J. Chem. Soc., 803 (1945); in Japanese patent application Laid-Open No. 26829/1983, etc. As another organic solvent, acetic acid is used in the former publication while a halogenated aliphatic hydrocarbon is employed in the latter publication.

The above-described conventional processes for the production of halobenzophenone derivatives are, however, accompanied by various problems. Namely, the process relying upon the oxidation with chromic acid consumes a large amount of chromic acid in the reaction. Further, it is necessary to cope with environmental problems including waste water disposal. This process therefore requires a significant cost so that it is difficult to industrially practice it under the circumstances.

On the other hand, the processes including the oxidation with nitric acid require the use of an organic solvent and therefore, substantial energy is needed for the recovery of the organic solvent. Besides, these processes still involve some unsolved environmental problems. For example, the use of a halogenated aliphatic hydrocarbon as solvent is accompanied by a problem, because there is a concern of deleterious influence to the environment so that more stringent limitations will certainly be imposed on its use in the future.

Regarding the processes relying upon oxidation with nitric acid, development of a new process is described as a substitute for the processes using an organic solvent, such as the processes as described above, from the viewpoints of economy and also environmental problems. From such viewpoints, one may consider directly oxidizing 1,1-dichloro-2,2-bis(4-chlorophenyl)ethylene with nitric acid for the production of 4,4'-dichlorobenzophenone without using any organic solvent. It has, however, been known that the nitric acid oxidation without an organic solvent results in the formation of nitrated substances, whereby the yield of 4,4'-dichlorobenzophenone as the target product is lowered (See O. G. Backeberg and J. L. C. Marais: J. Chem. Soc., 803 (1945)).

As has been described above, the use of an organic solvent is essential for the oxidation of 1,1-dichloro-2,2-bis(4-chlorophenyl)ethylene with nitric acid under the present circumstances. Thus, problems still remain unsolved from the viewpoints of economy and environmental problems.

SUMMARY OF THE INVENTION

This invention has been completed with the foregoing in view. It is an object of this invention to provide a process for easily producing halobenzophenone derivatives at a high yield without an organic solvent.

The present inventors have carried out an extensive investigation. As a result, it has been found that halobenzophenone derivatives represented by the following formula (II):

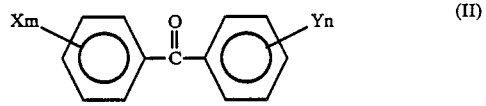

wherein X and Y are the same or different and are independently F, Cl, Br or I, m stands for an integer of from 1 to 4 and n stands for an integer of from 0 to 4, can be obtained in a short time and at a high yield without substantial formation of nitro compounds when an compound represented by the following formula (I):

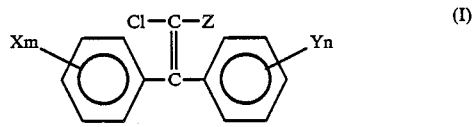

wherein X, Y, m and n have the same meanings as in the formula (II) and Z is H or Cl, is oxidized by using an aqueous nitric acid solution having a specific gravity in a particular range. The present invention has been brought to completion on the basis of this finding.

In one aspect of this invention, there is thus provided a process for the production of halobenzophenone derivatives represented by the formula (II). The process comprises oxidizing the compound represented by the formula (I) with an aqueous nitric acid solution having a specific gravity of from 1.32 to 1.47 as measured at 20° C. All specific gravities which will be described hereinafter are values as measured at the same temperature.

As will also become apparent from a comparison between Examples and Comparative Examples to be described subsequently, the process according to the present invention has such advantages as a substantially high conversion and a significantly high yield of the target product. In addition, according to this invention, halobenzophenones represented by the above formula (II) can be produced with ease at a high yield in the simplest reaction system composed of 1,1-dichloro-2,2-di(halophenyl)ethylene or 1-chloro-2,2-di(halophenyl)ethylene represented by the above formula (I), which is a reactant, and an aqueous solution of nitric acid. Further, this invention does not employ any organic solvent in the reaction system and therefore, the post-reaction operations for separation and purification are simple and economical compared with those of the conventional processes. According to this invention, halobenzophenones can be produced advantageously on an industrial scale.

DETAILED DESCRIPTION OF PREFERRED EMBODIMENTS

Compounds represented by the above-described formula (I) and used as reactants in the present invention include 1,1-dichloro-2-(halophenyl) -2-phenylethylene, 1,1-dichloro-2,2-di(halophenyl)ethylene, 1-chloro-2-(halophenyl)-2-phenylethylene and 1-chloro-2,2-di(-halophenyl)ethylene. The term "halophenyl" as used herein means a phenyl group having 1-4 halogen atoms selected from F, Cl, Br and I. Accordingly, a wide variety of compounds are included. In view of the application of these halobenzophenone derivatives, which are the target compounds of the present invention, as monomers for heat-resistant polymers, 1,1-dichloro-2,2-di(monohalophenyl)ethylenes and 1-chloro-2,2-di(-monohalophenyl)ethylenes are preferred as the reactants to be used in the present invention.

As specific examples of the above described reactants, the following isomers may be mentioned:
1,1-dichloro-2,2-di(fluorophenyl)ethylene;
1,1-dichloro-2-(bromophenyl)-2-(fluorophenyl)ethylene;
1,1-dichloro-2-(chlorophenyl)-2-(fluorophenyl)ethylene;
1,1-dichloro-2-(fluorophenyl)-2-(iodophenyl)ethylene;
1,1-dichloro-2,2-di(chlorophenyl)ethylene;
1,1-dichloro-2-(bromophenyl)-2-(chlorophenyl)ethylene;
1,1-dichloro-2-(chlorophenyl)-2-(iodophenyl)ethylene;
1,1-dichloro-2,2-di(bromophenyl)ethylene;
1,1-dichloro-2-(bromophenyl)-2-(iodophenyl)ethylene;
1,1-dichloro-2,2-di(iodophenyl)ethylene;
1-chloro-2,2-di(fluorophenyl)ethylene;
1-chloro-2-(bromophenyl)-2-(fluorophenyl)ethylene;
1-chloro-2-(chlorophenyl)-2-(fluorophenyl)ethylene;
1-chloro-2-(fluorophenyl)-2-(iodophenyl)ethylene;
1-chloro-2,2-di(chlorophenyl)ethylene;
1-chloro-2-(bromophenyl)-2-(chlorophenyl)ethylene;
1-chloro-2-(chlorophenyl)-2-(iodophenyl)ethylene;
1-chloro-2,2-di(bromophenyl)ethylene;
1-chloro-2-(bromophenyl)-2-(iodophenyl)ethylene; and
1-chloro-2,2-di(iodophenyl)ethylene.

In each of the above "bromophenyl, chlorophenyl, fluorophenyl and iodophenyl", one or more Br, Cl, F or I atoms may be bonded at any position on the phenyl group.

The ethylene moieties of the reactants listed above by way of example are oxidized by the process of the present invention, thereby obtaining benzophenone derivatives corresponding to the respective reactants. As representative examples of the halobenzophenone derivative represented by the formula (II) and obtained by the process of the present invention, 4,4-dichlorobenzophenone, 2,4'-dichlorobenzophenone and 4,4'-dibromobenzophenone may be mentioned by way of example.

As starting compounds represented by the formula (I), the following compounds can be used preferably:
1,1-dichloro-2,2-di(4-chlorophenyl)ethylene;
1-chloro-2,2-di(4-chlorophenyl)ethylene;
1,1-dichloro-2-(2-chlorophenyl)-2-(4-chlorophenyl)ethylene,
1-chloro-2-(2-chlorophenyl)-2-(4-chlorophenyl)ethylene,
1,1-dichloro-2,2-di(4-bromophenyl)ethylene; and
1-chloro-2,2-di(4-bromophenyl)ethylene.

In addition, the aqueous solution of nitric acid used in this invention is required to have a specific gravity in a range of from 1.32 to 1.47. At a specific gravity lower than 1.32, the reaction does not proceed. On the other hand, specific gravities higher than 1.47 tend to induce nitration as a side reaction. More preferably, the aqueous solution of nitric acid may range from 1.35 to 1.46.

The reaction temperature may range from −20° C. to 150° C. It is preferred to conduct the reaction at a lower temperature when the aqueous solution of nitric acid has a high specific gravity, but at a higher temperature when the aqueous solution of nitric acid has a low specific gravity. The temperature may range preferably from 0° C. to 120° C., and more preferably from 30° C. to 100° C.

The reaction time and the ratio of the reactant to the aqueous solution of nitric acid vary depending on the specific gravity of the aqueous solution of nitric acid and reaction temperature to be employed. The reaction time may usually range from 1 minute to hours, preferably from 5 minutes to 50 hours, and more preferably from 30 minutes to 15 hours. On the other hand, the weight ratio of the reactant to the aqueous solution of nitric acid ranges from 0.001 to 50, preferably from 0.005 to 5, more preferably from 0.01 to 1.

Although the reaction is usually performed under ordinary pressure, it may also be conducted under elevated pressure or under reduced pressure. The reaction can be conducted in an oxygen atmosphere, air atmosphere or inert gas atmosphere and no particular limitation is imposed on the reaction atmosphere. Moreover, as a reaction method, either a batchwise or continuous method can be used.

Where the main reaction product is 4,4'-dichlorobenzophenone or the like for example, it can be separated and recovered as crystals only by simply cooling the reaction mixture and collecting the crystals by filtration after completion of the reaction. Therefore, the present invention has an advantage that the post-reaction operations for separation and purification are easier compared with those of the conventional processes. Further, the reaction product can be obtained with a higher purity when the above operations are combined suitably with usual operations for separation and purification such as washing, extraction with an organic solvent, crystallization and vacuum distillation.

EXAMPLES

This invention will hereinafter be described specifically by the following Examples. It should however be borne in mind that this invention is not limited to or by the following Examples. Conversions and yields in the following Examples and Comparative Examples were calculated respectively in accordance with the following formulas:

$$\text{Conversion (\%)} = \frac{\text{Raw material charged (mole)} - \text{Remaining raw material (mole)}}{\text{Raw material charged (mole)}} \times 100$$

$$\text{Yield (\%)} = \frac{\text{Reaction product (mole)}}{\text{Raw material charged (mole)}} \times 100$$

EXAMPLE 1

A 200 ml flask fitted with a stirrer was charged with 5.0 g of 1,1-dichloro-2,2-bis(4-chlorophenyl)ethylene and then with 85 ml of an aqueous nitric acid solution having a specific gravity of 1.38. The weight ratio of the reactant to the aqueous solution of nitric acid was thus 0.043. While vigorously stirring the resulting mixture at 94° C. in a nitrogen gas atmosphere, their reaction was continued for 10 hours. The reaction mixture was thereafter cooled and crystals thus precipitated were extracted with dichloromethane. After the dichloromethane layer was sufficiently washed with water, the extract was quantitatively analyzed by gas chromatography. As a result, it was found that the conversion of 1,1-dichloro-2,2-bis(4-chlorophenyl)ethylene was 92.0% and the yield of 4,4'-dichlorobenzophenone was 66.0%.

EXAMPLE 2

A 200 ml flask fitted with a stirrer was charged with 5.0 g of 1,1-dichloro-2,2-bis(4-chlorophenyl)ethylene and then with 85 ml of an aqueous nitric acid solution having a specific gravity of 1.42. The weight ratio of the reactant to the aqueous solution of nitric acid was 0.041. While vigorously stirring the resulting mixture at 81° C. in a nitrogen gas atmosphere, their reaction was continued for 80 minutes. The reaction mixture was thereafter cooled and crystals thus precipitated were extracted with dichloromethane. After the dichloromethane layer was sufficiently washed with water, the extract was quantitatively analyzed by gas chromatography. As a result, it was found that the conversion of 1,1-dichloro-2,2-bis(4-chlorophenyl)ethylene was 100% and the yield of 4,4'-dichlorobenzophenone was 87.6%.

EXAMPLE 3

A 200 ml flask fitted with a stirrer was charged with 5.0 g of 1,1-dichloro-2,2-bis(4-chlorophenyl)ethylene and then with 85 ml of an aqueous nitric acid solution of having a specific gravity of 1.45. The weight ratio of the reactant to the aqueous solution of nitric acid was 0.041. While vigorously stirring the resulting mixture at 40° C. in a nitrogen gas atmosphere, their reaction was continued for 140 minutes. The reaction mixture was thereafter cooled and crystals thus precipitated were extracted with dichloromethane. After the dichloromethane layer was sufficiently washed with water, the extract was quantitatively analyzed by gas chromatography. As a result, it was found that the conversion of 1,1-dichloro-2,2-bis(4-chlorophenyl)ethylene was 100%, and the yield of 4,4'-dichlorobenzophenone was 91.3%.

EXAMPLE 4

A 200 ml flask fitted with a stirrer was charged with 5.0 g of 1-chloro-2,2-bis(4-chlorophenyl)ethylene and then with 85 ml of an aqueous nitric acid solution having a specific gravity of 1.42. The weight ratio of the reactant to the aqueous solution of nitric acid was 0.041. While vigorously stirring the resulting mixture at 65° C. in a nitrogen atmosphere, the reaction was continued for 1 hour. The reaction mixture was thereafter cooled and crystals thus precipitated were extracted with dichloromethane. After the dichloromethane layer was sufficiently washed with water, the extract was quantitatively analyzed by gas chromatography. As a result, it was found that the conversion of 1,1-dichloro-2,2-bis(4-chlorophenyl)ethylene was 91.0% and the yield of 4,4'-dichlorobenzophenone was 58.1%.

COMPARATIVE EXAMPLE 1

A reaction was continued for 25 hours under similar conditions to Example 1 except that an aqueous nitric acid solution having a specific gravity of 1.30 was used. The reaction mixture was thereafter cooled and extracted with dichloromethane. After the dichloromethane layer was sufficiently washed with water, the extract was quantitatively analyzed by gas chromatography. As a result, it was found that conversion of 1,1-dichloro-2,2-bis(4-chlorophenyl)ethylene was 4.2%, and no 4,4'-dichlorobenzophenone was formed at all.

COMPARATIVE EXAMPLE 2

A 200 ml flask equipped with a stirrer was charged with 3.3 g of 1,1-dichloro-2,2-bis(4-chlorophenyl)ethylene and then with 50 ml of an aqueous nitric acid solution having a specific gravity of 1.52. The weight ratio of the reaction material to the aqueous solution of nitric acid was 0.043. While vigorously stirring the resulting mixture at room temperature of about 20° C. in a nitrogen atmosphere, they were reacted for 1 hour. The reaction mixture was thereafter added with water, followed by extraction with dichloromethane. After sufficient washing of the dichloromethane layer with water, the extract was analyzed by gas chromatography. As a result, it was found that 1,1-dichloro-2,2-bis(4-chlorophenyl)ethylene was converted in its entirety to 4,4'-dichloro-3,3'-dinitrobenzophenone, but no 4,4'-dichlorobenzophenone was formed at all.

What is claimed is:

1. A process for the production of a halobenzophenone derivative represented by the following formula (II):

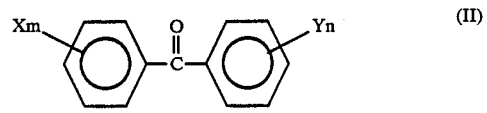

wherein X and Y are the same or different and are independently F, Cl, Br or I, m stands for an integer of from 1 to 4 and n stands for an integer of from 0 to 4, which comprises oxidizing a compound with an aqueous nitric acid solution having a specific gravity in a range of from 1.32 to 1.47 as measured at 20° C., and in the substantial absence of an organic solvent said compound being represented by the following formula (I):

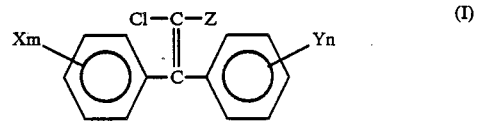

wherein X, Y, m and n have the same meanings as defined above and Z is Cl or H.

2. The process as claimed in claim 1, wherein a compound represented by the following formula:

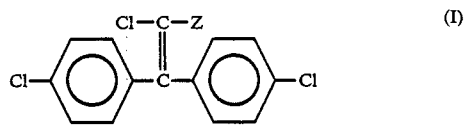

is oxidized with the aqueous nitric acid solution.

* * * * *